(12) United States Patent
Doan

(10) Patent No.: US 11,717,638 B2
(45) Date of Patent: Aug. 8, 2023

(54) METHOD FOR ANESTHETIZING THE LIPS

(71) Applicant: Thuy Doan, Atlanta, GA (US)

(72) Inventor: Thuy Doan, Atlanta, GA (US)

(73) Assignee: Thuy Doan, Atlanta, GA (US)

( * ) Notice: Subject to any disclaimer, the term of this patent is extended or adjusted under 35 U.S.C. 154(b) by 142 days.

(21) Appl. No.: 17/171,338

(22) Filed: Feb. 9, 2021

(65) Prior Publication Data

US 2022/0249799 A1    Aug. 11, 2022

(51) Int. Cl.
*A61M 19/00*    (2006.01)

(52) U.S. Cl.
CPC ....... *A61M 19/00* (2013.01); *A61M 2202/048* (2013.01); *A61M 2210/0606* (2013.01); *A61M 2210/0625* (2013.01)

(58) Field of Classification Search
CPC ............ A61M 19/00; A61M 2202/048; A61M 2210/0606; A61M 2210/0625; A61M 2210/06; A61Q 19/001; A61Q 19/08; A61B 2017/00792; A61F 2/0059
See application file for complete search history.

(56) References Cited

U.S. PATENT DOCUMENTS

| | | | |
|---|---|---|---|
| 5,817,090 A | 10/1998 | Abergel et al. | |
| 8,038,665 B2 | 10/2011 | Burgess | |
| 8,366,643 B2 | 2/2013 | Deem et al. | |
| 10,610,280 B1 | 4/2020 | Agha | |
| 10,624,840 B2 | 4/2020 | Breche | |
| 2003/0120307 A1* | 6/2003 | Abergel | A61B 17/29 623/902 |
| 2019/0184103 A1* | 6/2019 | Johnson | A61M 5/2448 |
| 2020/0101012 A1 | 4/2020 | Klein et al. | |
| 2020/0397750 A1 | 12/2020 | Klein et al. | |

FOREIGN PATENT DOCUMENTS

| | | | | |
|---|---|---|---|---|
| WO | WO-2014170921 A1 * | 10/2014 | ....... | A61B 17/06166 |
| WO | 2020082150 A1 | 4/2020 | | |

OTHER PUBLICATIONS

Isedeh, P. et al., Ensuring that injectable bicarbonate-buffered lidocaineepinephrine complies with 2015 United States Pharmacopeia (USP) compounding provisions, 2016, J Am Acad Dermatol, 75(2), pp. 454-455 (Year: 2016).*
Vent, Al. et al., Buffered lidocaine 1%/epinephrine 1:100,000 with sodium bicarbonate (sodium hydrogen carbonate) in a 3:1 ratio is less painful than a 9:1 ratio: A double-blind, randomized, placebo-controlled, crossover trial, 2020, J Am Acam Dermatol, 83(1), pp. 159-165 (Year: 2020).*
Afolabi, O. et al. "The effect of buffering on pain and duration of local anesthetic in the face: A double-blind, randomized controlled trial," Can J Plast Surg, 2013, vol. 21 No 4, pp. 209-212.
Joint Position Statement on "Safe in-office preparation of buffered lidocaine as a local anethetic," American Society for Dermatologic Surgery Association, 2019.

(Continued)

*Primary Examiner* — Katherine H Schwiker
*Assistant Examiner* — Hong-Van N Trinh
(74) *Attorney, Agent, or Firm* — Parker Poe Adams and Bernstein LLP

(57) ABSTRACT

The invention relates to a method for anesthetizing a patient's lips prior to a cosmetic procedure, such as lip augmentation or enhancement.

20 Claims, 1 Drawing Sheet

(56) References Cited

OTHER PUBLICATIONS

Brandis, K. "Alkalinisation of local anaesthetic solutions," Retrieved from www.australianprescriber.com, Australian Prescriber, 2011, vol. 34 No 6, pp. 173-175.
Dermatologist, "Optimal mixing ratio reduces pain during lido/epi injection," J Am Acad Dermatol., Jan. 2020.
Finsen, V. "Reduced pain when injecting lidocaine—Pain on injection of lidocaine is often considered a necessary evil, but it can be reduced by simple means," Clinical Review, Tidsskr Nor Legeforen nr. 9, 2017, 137, pp. 629-630.
Frank S.G. et al. "How acidic is the lidocaine we are injecting and how much bicarbonate should we add?," Original Article, Can J Plast Surg, 2012, 20(2), pp. 71-74.
Sedeh, P. et al. "Ensuring that injectable bicarbonate-buffered lidocaine-epinephrine complies with 2015 United States Pharmacopeia (USP) compounding provisions," J Am Acad Dermatol, 2016, 75(2), pp. 454-455.
Katzen J.T. et al. "Surgical and nonsurgical options to plump up your lips," American Society of Plastivc Surgeons, New Blog, 2017, pp. 35-39.
Malamed, S.F. et al. "Faster onset and more comfortable injection with alkalinized 2% lidocaine with epinephrine 1:100,000," Compendium, Special Issue, 2013, vol. 34, Issue 2.
Phero, J.A. et al. "Buffered versus non-buffered lidocaine with epinephrine for mandibular nerve block: Clinical outcomes," Randomized Controlled Trial, J Oral Maxillofac Surg. 2017, 75(4), pp. 688-693.
Stewart, J.H et al. "Neutralized lidocaine with epinephrine for local anesthesia—II," Comparative Study, J Dermatol Surg Oncol. 1990, 16(9), pp. 842-845.
Vent, A. et al. "Buffered lidocaine 1%/epinephrine 1:100,000 with sodium bicarbonate (sodium hydrogen carbonate) in a 3:1 ratio is less painful than a 9:1 ratio: A doubleblind, randomized, placebo-controlled, crossover trial," J Am Acad Dermatol., 2020, 83(1), pp. 159-165.

\* cited by examiner

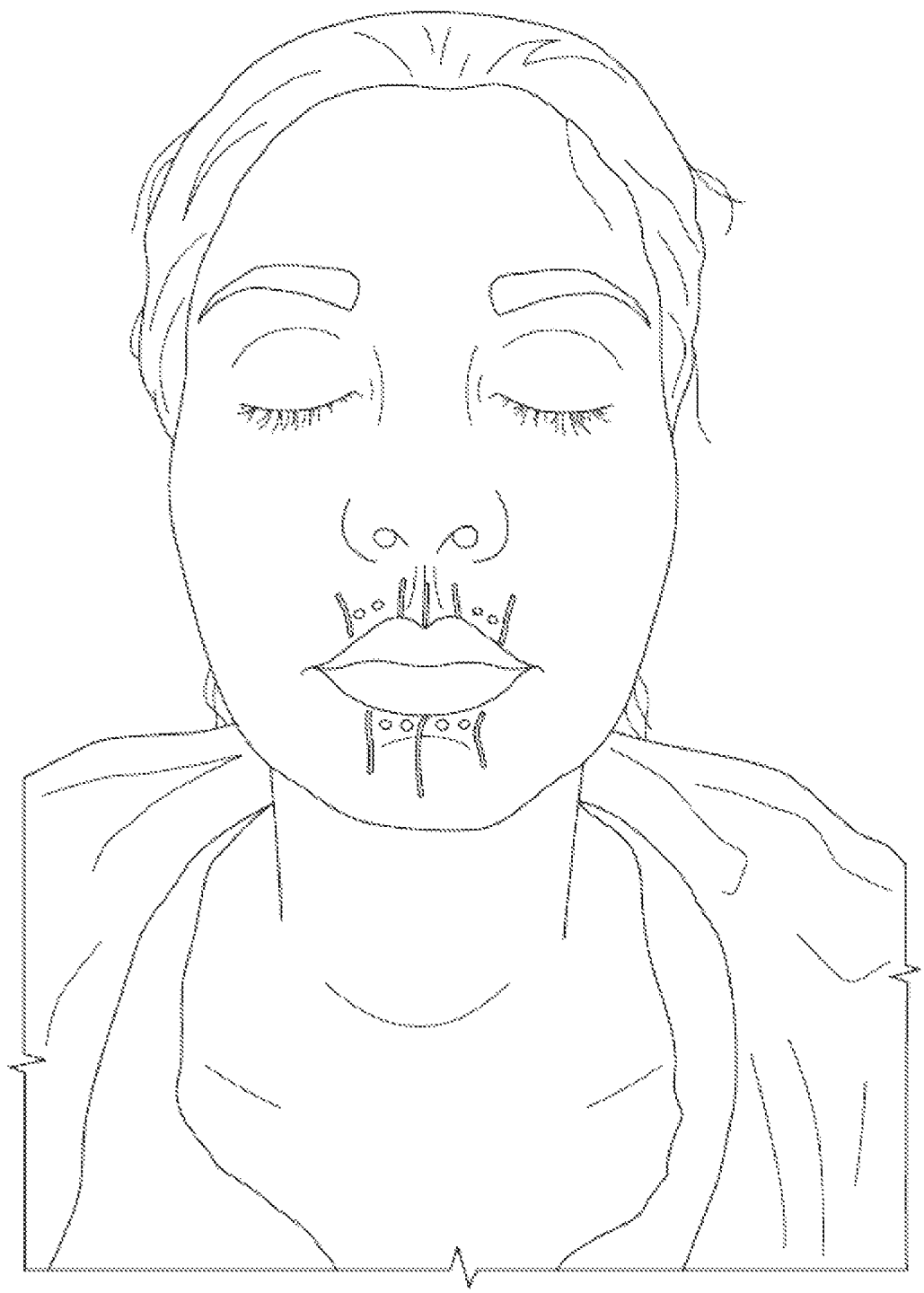

METHOD FOR ANESTHETIZING THE LIPS

BACKGROUND OF THE INVENTION

The present invention relates to methods for anesthetizing a patient's lips prior to a cosmetic procedure, such as lip augmentation or enhancement.

DESCRIPTION OF RELATED ART

Lip size and shape are facial features, which directly impact attractiveness levels. A person's lip shape and smile are an indicator of their beauty. In today's culture, full, plump lips are considered attractive. Thus, many individuals seek out methods to increase the fullness of their lips. Because of the desire for fuller lips, procedures have been developed to enlarge and/or alter the shape of a person's lips. These procedures involve injecting or implanting various types of materials into the lips, thereby plumping them.

A variety of materials and methods are used for lip augmentation. A current technique to provide lip augmentation involves injecting a dermal filler, such as fat, collagen, hyaluronic acid, or particulated dermis or fascia into the lip. Examples of commercially available dermal fillers include Juvederm Ultra-XC, Juvederm Volbella®, Belotero Balance®, Restylane Kysse, and Restylane Silk. The effect of using dermal fillers, however, are not permanent and one or more repeat course of treatment are typically necessary to restore the look of the patient's lips. Injecting a dermal filler is the most commonly used method for lip augmentation or enhancement.

Other techniques, such as liquid silicone injections, provide for more permanent lip augmentation. However, liquid silicone injections carry the potential for various problems, such as skin ulceration, long-term nodularity and granuloma formation, and chronic cellulitis. Additionally, it is difficult to remove liquid silicone from the lips should a problem arise or should the patient desire removal. Thus, silicon injections are rarely used today.

More permanent lip augmentation techniques involve implanting various forms of expanded polytetraflouroethylene (PTFE) such as Gore-Tex® strips or tubular forms of PTFE, such as Softform® and Ultrasoft™. Expanded PTFE utilizes the concept of tissue ingrowth into the porous wall of the implant. While beneficial in some areas of the body, implantation of such material into the lips can be detrimental due to tissue adherence to the implant, which often results in a restriction of lip excursion with an abnormal appearance of facial expression. Furthermore, fluid may accumulate in the tubular forms of PTFE, thereby resulting in an unacceptably high incidence of infection with subsequent loss of the implant.

Patients who undergo cosmetic injections for lip enhancement feel more confident after the procedure and have a renewed sense of attractiveness.

Lip injections, however, can be somewhat painful. Since the lips are innervated with many nerves they are a very sensitive area to be injected with a filler. Thus, lip enhancement procedures routinely involves administering a local anesthetic prior to injecting the lip filler.

To numb the lips a topical anesthetic can be applied to the lips. Topical anesthetics, however, provides only minimal numbing of the lips and, therefore, are minimally effective.

Local injection of anesthesia in the area of the lips can also be used to effect numbness of the lips. For example, dental blocks and nerve blocks can be used numb the lips.

Dental blocks involve injecting anesthesia intraorally (to the gums under the lip). Dental blocks, however, require administering a large volume of anesthesia and, while numbing a large area of the face, do not provide complete numbness to the desired area. Numbness from a dental blocks also takes a long time to wear off. Moreover, in addition to numbing the lips, a dental block affects motor function so that the patient cannot smile or talk, often for hours.

Nerve blocks involve numbing the lips by injecting anesthesia extraorally (outside the mouth) around the nerves that innervate the lips. To numb the upper lip, anesthesia is injected near the nostrils to block pain signals from the infraorbital nerve. Blocking pain signals from the infraorbital nerve, however, in addition to numbing the upper lip also numbs the lower eyelid, the side of the nose, and the upper lip.

To numb the lower lip, anesthesia is injected just off the midline of the chin to block pain signals from the mental nerve. In addition to numbing the lower lip, blocking pain signals from the mental nerve also numbs the chin.

Current methods of inducing numbness by local injection, however, require large volumes of anesthetic, which can be problematic for lip filler procedures as they can distort the anatomy of the lips, making it harder to properly apply the lip fillers in the designated areas. Current methods of inducing numbness by local injection are also uncomfortable because, in addition to numbing the lips, numb a large area of the face. Current methods of inducing numbness by local injection also take a long time to wear off.

Commonly used anesthetics are lidocaine, bupivacaine, and mepivacaine, which can be administered with or without epinephrine. Epinephrine is a vasoconstrictor.

Thus, there is a need in the art for better methods of administering local anesthesia to a patient's lips prior to a cosmetic procedure, such as lip augmentation or enhancement.

SUMMARY OF THE INVENTION

The invention is directed to a method for anesthetizing a patient's lips prior to a cosmetic procedure, such as lip augmentation or enhancement.

One embodiment of the invention is directed to a method for anesthetizing the upper lip of a patient. The method involves administering 4 injections of an anesthetic solution (2 injections on the left side of the upper lip and 2 injections on the right side of the upper lip).

The method for anesthetizing the upper lip of a patient comprises:

administering a first injection of an anesthetic solution lateral to the left side of the philtrum, administering a second injection of the anesthetic solution to the left of the first injection and separated from the first injection by a gap of about 0.1 cm, administering a third injection of the anesthetic solution lateral to the right side of the philtrum, and administering a fourth injection of the anesthetic solution to the right of the third injection and separated from the third injection by a gap of about 0.1 cm;

wherein each injection is administered in close proximity to the vermillion border of the upper lip, and wherein the volume of each injection ranges from about 0.05 to about 0.1 mL.

One embodiment of the invention is directed to a method for anesthetizing the lower lip of a patient. The method involves administering 4 injections of an anesthetic solution (2 injections on the left side of the lower lip and 2 injections on the right side of the lower lip).

The method for anesthetizing the lower lip of a patient comprises:

administering a first injection, a second injection, a third injection, and a fourth injection of an anesthetic solution, wherein each injection is administered in close proximity to the vermillion border of the lower lip, wherein the four injections are centered around the medial aspect of the lower lip, are approximately evenly spaced apart, and the width between the first injection and the fourth injection is about 1 inch, and wherein the volume of each injection ranges from about 0.05 to about 0.1 mL.

One embodiment of the invention is directed to a method for anesthetizing the upper and lower lips of a patient. The method involves administering 8 injections of an anesthetic solution (2 injections on the left side of the upper lip, 2 injections on the right side of the upper lip, 2 injections on the left side of the lower lip and 2 injections on the right side of the lower lip).

The method for anesthetizing the upper lip and lower lip of a patient comprises:

administering a first injection of an anesthetic solution lateral to the left side of the philtrum, administering a second injection of the anesthetic solution to the left of the first injection and separated from the first injection by a gap of about 0.1 cm, administering a third injection of the anesthetic solution lateral to the right side of the philtrum, administering a fourth injection of the anesthetic solution to the right of the third injection and separated from the third injection by a gap of about 0.1 cm, wherein each of the first, second, third, and fourth injections are administered in close proximity to the vermillion border of the upper lip; and administering a fifth injection, a sixth injection, a seventh injection, and an eighth injection of the anesthetic solution, wherein the fifth, sixth, seventh, and eighth injections are administered in close proximity to the vermillion border of the lower lip, wherein the fifth, sixth, seventh, and eighth injections are centered around the medial aspect of the lower lip, are approximately evenly spaced apart, and the width between the first injection and the fourth injection is about 1 inch, and wherein the volume of each injection ranges from about 0.05 to about 0.1 mL.

BRIEF DESCRIPTIONS OF THE FIGURES

FIG. 1 depicts the location of the injections according to the method of the invention. The circles indicate the location of the injections to numb the upper lip and the lower lip.

DETAILED DESCRIPTION OF THE INVENTION

Definitions

The phrase "2% drug," as used herein, means 2000 mg of a drug in 100 mL of solution. For example, the phrase "2% lidocaine" means 2000 mg of lidocaine in 100 mL of solution.

The phrase "X:Y epinephrine," as used herein, means X g epinephrine in Y mL of solution. For example, the phrase "1:100,000 epinephrine" means 1 g epinephrine in 100,000 mL of solution.

The phrase "8.4% sodium bicarbonate," as used herein, means 84 mg of sodium bicarbonate ($NaHCO_3$) in 1 mL of solution.

The term "philtrum," as used herein, has its typical anatomical meaning, i.e., the midline groove in the upper lip that runs from the top of the lip to the nose.

The term "vermilion border," as used herein, has its typical anatomical meaning, i.e., the rim of paler skin that demarcates the vermilion from the surrounding skin.

The Method for Administering Anesthesia

The invention is directed to a method for or anesthetizing a patient's lips prior to a cosmetic procedure, such as lip augmentation or enhancement.

In one embodiment, the method is directed to anesthetizing the upper lip of a patient. The method involves administering 4 injections of an anesthetic solution (2 injections on the left side of the upper lip and 2 injections on the right side of the upper lip).

The method for anesthetizing the upper lip of a patient comprises:

administering a first injection of an anesthetic solution lateral to the left side of the philtrum, administering a second injection of the anesthetic solution to the left of the first injection and separated from the first injection by a gap of about 0.1 cm, administering a third injection of the anesthetic solution lateral to the right side of the philtrum, and administering a fourth injection of the anesthetic solution to the right of the third injection and separated from the third injection by a gap of about 0.1 cm;

wherein each injection is administered in close proximity to the vermillion border of the upper lip, and wherein the volume of each injection ranges from about 0.05 to about 0.1 mL.

If the upper lip of the patient is asymmetric the method can further comprise administering a fifth injection, wherein the fifth injection is administered on the side of the asymmetry about 0.5 cm lateral to the injection farthest from the philtrum (i.e., either to the left of the second injection or to the right of the fourth injection). The fifth injection should not be more than about 1 cm lateral to the injection farthest from the philtrum so as to avoid bruising by contact with the superior labial artery.

Preferably the volume of each injection ranges from about 0.05 to about 0.07 mL. More preferably the volume of each injection is about 0.06 mL.

In a preferred embodiment of the method of anesthetizing the upper lip of a patient, the volume of each injection is about 0.06 mL and the anesthetic solution is lidocaine HCL 2% and epinephrine 1:100,000 combined with 8.4% sodium bicarbonate, wherein the ratio of lidocaine HCL 2% and epinephrine 1:100,000 to 8.4% sodium bicarbonate is about 5:1 (v/v).

In another embodiment, the invention is directed to a method for anesthetizing the lower lip of a patient. The method involves administering 4 injections of an anesthetic solution (2 injections on the left side of the lower lip and 2 injections on the right side of the lower lip).

The method for anesthetizing the lower lip of a patient comprises:

administering a first injection, a second injection, a third injection, and a fourth injection of an anesthetic solution, wherein each injection is administered in close proximity to the vermillion border of the lower lip, wherein the four injections are centered around the medial aspect of the lower lip, are approximately evenly spaced apart, and the width between the first injection and the fourth injection is about 1 inch, and wherein the volume of each injection ranges from about 0.05 mL to about 0.1 mL.

If the lower lip of the patient is asymmetric the method can further comprise administering a fifth injection, wherein the fifth injection is administered on the side of the asymmetry about 0.5 cm lateral to the injection farthest from the medial aspect of the lower lip. The fifth injection should not be more than about 1 cm lateral to the injection farthest from the medial aspect of the lower lip so as to avoid bruising by contact with the inferior labial artery.

Preferably the volume of each injection ranges from about 0.05 mL to about 0.07 mL. More preferably the volume of each injection is about 0.06 mL.

In a preferred embodiment of the method of anesthetizing the lower lip of a patient, the volume of each injection is about 0.06 mL and the anesthetic solution is lidocaine HCL 2% and epinephrine 1:100,000 combined with 8.4% sodium bicarbonate, wherein the ratio of lidocaine HCL 2% and epinephrine 1:100,000 to 8.4% sodium bicarbonate is about 5:1 (v/v).

In another embodiment, the invention is directed to a method for anesthetizing the upper and lower lips of a patient. The method involves administering 8 injections of an anesthetic solution (2 injections on the left side of the upper lip, 2 injections on the right side of the upper lip, 2 injections on the left side of the lower lip and 2 injections on the right side of the lower lip).

The method for anesthetizing the upper lip and lower lip of a patient comprises:

administering a first injection of an anesthetic solution lateral to the left side of the philtrum, administering a second injection of the anesthetic solution to the left of the first injection and separated from the first injection by a gap of about 0.1 cm, administering a third injection of the anesthetic solution lateral to the right side of the philtrum, administering a fourth injection of the anesthetic solution to the right of the third injection and separated from the third injection by a gap of about 0.1 cm;

wherein each of the first injection, the second injection, the third injection, and the fourth injection are administered in close proximity to the vermillion border of the upper lip, and administering a fifth injection, a sixth injection, a seventh injection, and an eighth injection of the anesthetic solution, wherein the fifth, sixth, seventh, and eighth injections are administered in close proximity to the vermillion border of the lower lip, wherein the fifth, sixth, seventh, and eighth injections are centered around the medial aspect of the lower lip, are approximately evenly spaced apart, and the width between the first injection and the fourth injection is about 1 inch, and wherein the volume of each injection ranges from about 0.05 to about 0.1 mL.

If the lower lip or upper lip of the patient is asymmetric the method can further comprise administering a ninth injection to the lower lip or the upper lip. If the ninth injection is administered to the lower lip, the ninth injection is administered on the side of the asymmetry about 0.5 cm lateral to the injection farthest from the medial aspect of the lower lip and should not be more than about 1 cm lateral to the injection farthest from the medial aspect of the lower lip so as to avoid bruising by contact with the inferior labial artery. If the ninth injection is administered to the upper lip, the ninth injection is administered on the side of the asymmetry about 0.5 cm lateral to the injection farthest from the philtrum (i.e., either to the left of the second injection or to the right of the fourth injection) and should not be more than about 1 cm lateral to the injection farthest from the philtrum so as to avoid bruising by contact with the superior labial artery.

Preferably the volume of each injection ranges from about 0.05 to about 0.07 mL. More preferably the volume of each injection is about 0.06 mL.

In a preferred embodiment of the method of anesthetizing the upper lip and the lower lip of a patient, the volume of each injection is about 0.06 mL and the anesthetic solution is lidocaine HCL 2% and epinephrine 1:100,000 combined with 8.4% sodium bicarbonate, wherein the ratio of lidocaine HCL 2% and epinephrine 1:100,000 to 8.4% sodium bicarbonate is about 5:1 (v/v).

Suitable anesthetics for injection include, but are not limited to, lidocaine, bupivacaine, and mepivacaine. The anesthetic can be administered with or without epinephrine. Illustrative commercially available injectable anesthetics include: lidocaine HCl 2%; lidocaine HCl 2% and epinephrine 1:100,000; lidocaine HCl 2% and epinephrine 1:50,000; lidocaine HCl 1% and epinephrine 1:100,000; bupivacaine HCl 0.25% and epinephrine 1:200,000; bupivacaine HCl 0.5% and epinephrine 1:200,000; and mepivicaine HCl 1%, 1.5%, 2%, or 3%. In a preferred embodiment, the anesthetic is lidocaine HCl 2% and epinephrine 1:100,000

In a preferred embodiment, sodium bicarbonate, such as 8.4% sodium bicarbonate, is added to the anesthetic to provide the anesthetic solution. Adding sodium bicarbonate to the anesthetic reduces pain associated with administering the anesthetic. Without wishing to be bound be theory, it is believed that the sodium bicarbonate reduces the pain by reducing the acidity of the anesthetic. In one embodiment, the ratio of anesthetic to 8.4% sodium bicarbonate solution ranges from about 3:1 to about 10:1 (v/v), for example. about 3:1 to 6:1 (v/v). In one embodiment, the ratio of anesthetic to 8.4% sodium bicarbonate solution is about 5:1 (v/v).

In a preferred embodiment, the anesthetic solution is lidocaine HCl 2% and epinephrine 1:100,000 combined with 8.4% sodium bicarbonate, wherein the ratio of lidocaine HCl 2% and epinephrine 1:100,000 to 8.4% sodium bicarbonate ranges from about 3:1 to 6:1 (v/v), more preferably about 5:1 (v/v).

The volume of each injection ranges from about 0.05 mL to about 0.1 mL, preferably from about 0.05 mL to about 0.07 mL, more preferably about 0.06 mL.

In a preferred embodiment, the anesthetic is lidocaine HCl 2% and epinephrine 1:100,000 combined with 8.4% sodium bicarbonate, wherein the ratio of lidocaine HCl 2% and epinephrine 1:100,000 to 8.4% sodium bicarbonate is about 5:1 (v/v) and the volume of each injection ranges from about 0.05 mL to about 0.1 mL, preferably about 0.05 mL to about 0.07 mL, more preferably about 0.06 mL.

Thus, when numbing only the upper lip (or only the lower lip), the method involves administering a total injection volume (i.e., 4 injections) of from about 0.2 mL to about 0.4 mL. For example, when the volume of each injection is about 0.06 mL, the total injection volume is about 0.24 mL (i.e., 0.06 mL/injection×4 injections). When numbing both the upper and lower lips, the method involves administering a total injection volume (i.e., 8 injections) of from about 0.4 mL to about 0.8 mL. For example, when the volume of each injection is about 0.06 mL, the total injection volume is about 0.48 mL (i.e., 0.06 mL/injection×8 injections).

Typically, the anesthetic solution is injected using a syringe having a volume of about 1 mL connected to a ½ inch needle with a gauge greater than 30, such as ½ inch 32 gauge needle, such as are commercially available from TSK Laboratories of the Netherlands. The needle is inserted parallel (not perpendicular) to the lip tissue so as to assure that the anesthetic is administered in the same direction the needle is entering and that the anesthetic can exit when the lip filler is injected.

In one embodiment, the bevel of the needle is inserted and held for about three seconds and the needle then slowly inserted to a depth of about one-half of the needle length. After about one-half of the needle has been inserted, about 0.016 mL to about 0.033 mL of anesthetic solution is ejected from the syringe, about 3 seconds is allowed to elapse, another about 0.016 mL to about 0.03 3 mL of anesthetic solution is ejected from the syringe, another about 3 seconds is allowed to elapse, another about 0.016 mL to about 0.033 mL of anesthetic solution is ejected from the syringe and the syringe then withdrawn, so as to administer a total volume of anesthetic solution of from about 0.05 mL to about 0.1 mL.

In one embodiment, the bevel of the needle is inserted and held for about three seconds and the needle then slowly inserted to a depth of about one-half of the needle length. After about one-half of the needle has been inserted, about 0.2 mL of anesthetic solution is ejected from the syringe, about 3 seconds is allowed to elapse, another about 0.2 mL of anesthetic solution is ejected from the syringe, another about 3 seconds is allowed to elapse, another about 0.2 mL of anesthetic solution is ejected from the syringe and the syringe then withdrawn, so as to administer a total volume of anesthetic solution of about 0.06 mL.

The method provides effective numbing of the lips so as to minimize or eliminate pain associated with administering the lip filler.

The method, by injecting only a small volume of anesthesia, provides effective anesthesia yet advantageously minimizes swelling, bruising, redness, and distortion of the lips. The method also advantageously provides effective local numbing of the lips without significant numbing of other areas of the face, such as the nose, eyelid, and chin. Also, the numbness advantageously wears off quickly, typically within less than about 2 hours.

EXAMPLES

The following testimonials are from patients who received injections of lip fillers after having their lips anesthetized by the method described herein. Each of the patients had previously received injections of lip fillers after having their lips anesthetized by a procedure that involved topical application of anesthesia, a dental block, or a nerve block.

Example 1: Patient 1 had been getting lip injections for years with a procedure wherein the lips were numbed using a topical anesthetic. When patient 1 received lip injections wherein the lips were numbed using the above described method, the patient commented: With topical anesthesia I can still feel all the needle pokes despite given 20 mins of topical numbing. With your technique, I feel almost zero pain.

Example 2: Patient 2 had been getting lip injections for years with a procedure wherein the lips were numbed using a dental block. When patient 2 received lip injections wherein the lips were numbed using the above described method the patient commented: Despite getting the dental block, sometimes it does not cover the whole lips and I can still feel the pain. With your technique, the only part I feel is a pinch in the center of the lips, otherwise, I don't feel any pain Example 3: Patient 3 had been getting lip injections for years with a procedure wherein the lips were numbed using a pyriform nerve block and a mental nerve block. When patient 3 received lip injections wherein the lips were numbed using the above described method the patient commented: When injectors numb from the outside near my nose and chin, it numbs the whole half of my lower face. I like how yours only numbs the lips. This technique only last for 1.5 hours and then it goes away. The previous would numb for 3-4 hours.

While the present invention has been related in terms of the foregoing embodiments, those skilled in the art will recognize that the invention is not limited to the embodiments described. The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof. Any embodiments that are functionally equivalent are within the scope of this invention. Indeed, various modifications of the invention in addition to those shown and described herein will become apparent to those skilled in the art and are intended to fall within the scope of the appended claims. Such variations of the invention, including the substitution of all equivalents now known or later developed, which would be within the purview of those skilled in the art, and changes in formulation or minor changes in experimental design, are to be considered to fall within the scope of the invention incorporated herein.

What is claimed is:

1. A method for anesthetizing an upper lip of a patient having a philtrum and a vermillion border comprising:
   (i) administering a first injection of an anesthetic solution lateral to a left side of the philtrum,
   (ii) administering a second injection of the anesthetic solution to the left of the first injection and separated from the first injection by a gap of about 0.1 cm,
   (iii) administering a third injection of the anesthetic solution lateral to a right side of the philtrum, and
   (iv) administering a fourth injection of the anesthetic solution to the right of the third injection and separated from the third injection by a gap of about 0.1 cm;
   wherein each injection is administered in close proximity to the vermillion border of the upper lip, each injection is made using a beveled needle, and
   wherein the first injection, second injection, third injection, and fourth injection each have a volume that ranges from about 0.05 mL to about 0.1 mL.

2. The method of claim 1, wherein the volume of the first injection, second injection, third injection, and fourth injection each ranges from about 0.05 mL to about 0.07 mL.

3. The method of claim 2, wherein the volume of the first injection, second injection, third injection, and fourth injection are each about 0.06 mile.

4. The method of claim 1, wherein the anesthetic solution is lidocaine HCL 2% and epinephrine 1:100,000 combined with 8.4% sodium bicarbonate.

5. The method of claim 1, wherein the anesthetic solution is lidocaine HCL 2% and epinephrine 1:100,000 combined with 8.4% sodium bicarbonate, having a ratio of lidocaine HCL 2% and epinephrine 1:100,000 to 8.4% sodium bicarbonate that ranges from about 3:1 to 6:1 (v/v), and the volume of the first injection, second injection, third injection, and fourth injection are each about 0.06 mL.

6. The method of claim 5, wherein the ratio of lidocaine HCL 2% and epinephrine 1:100,000 to 8.4% sodium bicarbonate is about 5:1 (v/v).

7. The method of claim 1, wherein the anesthetic solution is injected using a syringe having a volume of about 1 mL connected to the beveled needle, the beveled needle being a ½ inch needle with a gauge greater than 30.

8. The method of claim 7, wherein the beveled needle is inserted parallel to tissue of the upper lip to a depth of about one-half of the beveled needle length.

9. A method for anesthetizing a lower lip of a patient having a philtrum, a vermillion border, and a medial aspect comprising:
administering a first injection, a second injection, a third injection, and a fourth injection of an anesthetic solution,
wherein each injection is administered in close proximity to the vermillion border of the lower lip,
wherein the four injections are centered around the medial aspect of the lower lip, are approximately evenly spaced apart, and having a width between the first injection and the fourth injection that is about 1 inch,
wherein each injection is made using a beveled needle, and
wherein the first injection, second injection, third injection, and fourth injection each have a volume that ranges from about 0.05 mL to about 0.1 mL.

10. The method of claim 9, wherein the volume of each injection ranges from about 0.05 mL to about 0.07 mL.

11. The method of claim 10, wherein the volume of each injection is about 0.06 mL.

12. The method of claim 9, wherein the anesthetic solution is lidocaine HCL 2% and epinephrine 1:100,000 combined with 8.4% sodium bicarbonate.

13. The method of claim 9, wherein the anesthetic solution is lidocaine HCL 2% and epinephrine 1:100,000 combined with 8.4% sodium bicarbonate, having a ratio of lidocaine HCL 2% and epinephrine 1:100,000 to 8.4% sodium bicarbonate that ranges from about 3:1 to 6:1 (v/v), and the volume of the first injection, second injection, third injection, and fourth injection are each about 0.06 mL.

14. The method of claim 13, wherein the ratio of lidocaine HCL 2% and epinephrine 1:100,000 to 8.4% sodium bicarbonate is about 5:1 (v/v).

15. A method for anesthetizing an upper lip and a lower lip of a patient having a philtrum, a vermillion border, and a medial aspect:

(i) administering a first injection of an anesthetic solution lateral to a left side of the philtrum,
(ii) administering a second injection of the anesthetic solution to the left of the first injection and separated from the first injection by a gap of about 0.1 cm,
(iii) administering a third injection of the anesthetic solution lateral to a right side of the philtrum,
(iv) administering a fourth injection of the anesthetic solution to the right of the third injection and separated from the third injection by a gap of about 0.1 cm;
wherein each of the first injection, the second injection, the third injection, and the fourth injection are administered in close proximity to the vermillion border of the upper lip, and
(v) administering a fifth injection, a sixth injection, a seventh injection, and an eighth injection of the anesthetic solution,
wherein the fifth, sixth, seventh, and eighth injections are administered in close proximity to the vermillion border of the lower lip,
wherein the fifth, sixth, seventh, and eighth injections are centered around the medial aspect of the lower lip, are approximately evenly spaced apart, and having a width between the first injection and the fourth injection that is about 1 inch,
wherein each injection is made using a beveled needle, and
wherein the first injection, second injection, third injection, fourth injection, fifth injection, sixth injection, seventh injection, and eighth injection each have a volume that ranges from about 0.05 mL to about 0.1 mL.

16. The method of claim 15, wherein the volume of each injection ranges from about 0.05 mL to about 0.07 mL.

17. The method of claim 16, wherein the volume of each injection is about 0.06 mL.

18. The method of claim 15, wherein the anesthetic solution is lidocaine HCL 2% and epinephrine 1:100,000 combined with 8.4% sodium bicarbonate.

19. The method of claim 15, wherein the anesthetic solution is lidocaine HCL 2% and epinephrine 1:100,000 combined with 8.4% sodium bicarbonate, having a ratio of lidocaine HCL 2% and epinephrine 1:100,000 to 8.4% sodium bicarbonate ranges from about 3:1 to 6:1 (v/v), and the volume of each injection is about 0.06 mL.

20. The method of claim 19, wherein the ratio of lidocaine HCL 2% and epinephrine 1:100,000 to 8.4% sodium bicarbonate is about 5:1 (v/v).

* * * * *